United States Patent [19]

Unger

[11] Patent Number: 5,874,208
[45] Date of Patent: Feb. 23, 1999

[54] METHOD AND APPARATUS FOR HARVESTING BLOOD COMPONENTS

[75] Inventor: Peter Unger, Stockholm, Sweden

[73] Assignee: Omega Mediciteknik AB, Stockholm, Sweden

[21] Appl. No.: 913,682

[22] PCT Filed: Mar. 21, 1996

[86] PCT No.: PCT/SE96/00356

§ 371 Date: Sep. 22, 1997

§ 102(e) Date: Sep. 22, 1997

[87] PCT Pub. No.: WO96/29081

PCT Pub. Date: Sep. 26, 1996

[30] Foreign Application Priority Data

Mar. 21, 1995 [SE] Sweden ................................ 9500999

[51] Int. Cl.$^6$ .............................. A01N 1/02; B01D 35/14; B01D 21/24; B01D 24/38
[52] U.S. Cl. ................................ 435/2; 210/86; 210/109; 210/94; 210/143; 222/513; 222/23; 222/52; 222/95; 222/96; 222/103; 222/214
[58] Field of Search ................................. 435/2; 210/86, 210/109, 94, 143; 222/513, 23, 52, 95, 96, 103, 214

[56] References Cited

U.S. PATENT DOCUMENTS

| 4,359,005 | 11/1982 | Greenblatt | 614/141 |
|---|---|---|---|
| 4,663,032 | 5/1987 | Loos et al. | 210/97 |
| 4,976,851 | 12/1990 | Tanokura et al. | 210/86 |
| 5,045,185 | 9/1991 | Ohnaka et al. | 210/86 |
| 5,135,646 | 8/1992 | Tanokura et al. | 210/109 |
| 5,207,645 | 5/1993 | Ross et al. | 604/141 |

FOREIGN PATENT DOCUMENTS

| 0 161 551 | 11/1985 | European Pat. Off. . |
|---|---|---|
| 3417892 | 11/1985 | Germany . |

*Primary Examiner*—Lynette F. Smith
*Assistant Examiner*—Brett Nelson
*Attorney, Agent, or Firm*—Jacobson, Price, Holman & Stern, PPLC

[57] ABSTRACT

A method and an extractor for pressing out plasma and buffy coat from a collapsible blood container (1), in which blood has been divided, by centrifugation, into a plasma layer, a buffy coat layer and a layer of red blood cells. The plasma and then the buffy coat are pressed out each through a separate outlet tube (2) or through a common outlet tube (2), which is connected to the top portion of the blood container, a pulsating pressure being applied to a top section of the blood container (1) during the end phase of the pressing-out of buffy coat. The extractor has a stationary support surface (6) and a movable pressing member (7), between which the blood container is suspended and subjected to a compressive force in order to press out the plasma and then the buffy coat through the outlet tube (2). The extractor has one or more inflatable cushions (12, 13) arranged on the support surface (6) or the pressing member (7) or both on the same level as the top section of the blood container (1), and a device (15, 16) for pulsating the pressure in said cushions.

8 Claims, 1 Drawing Sheet

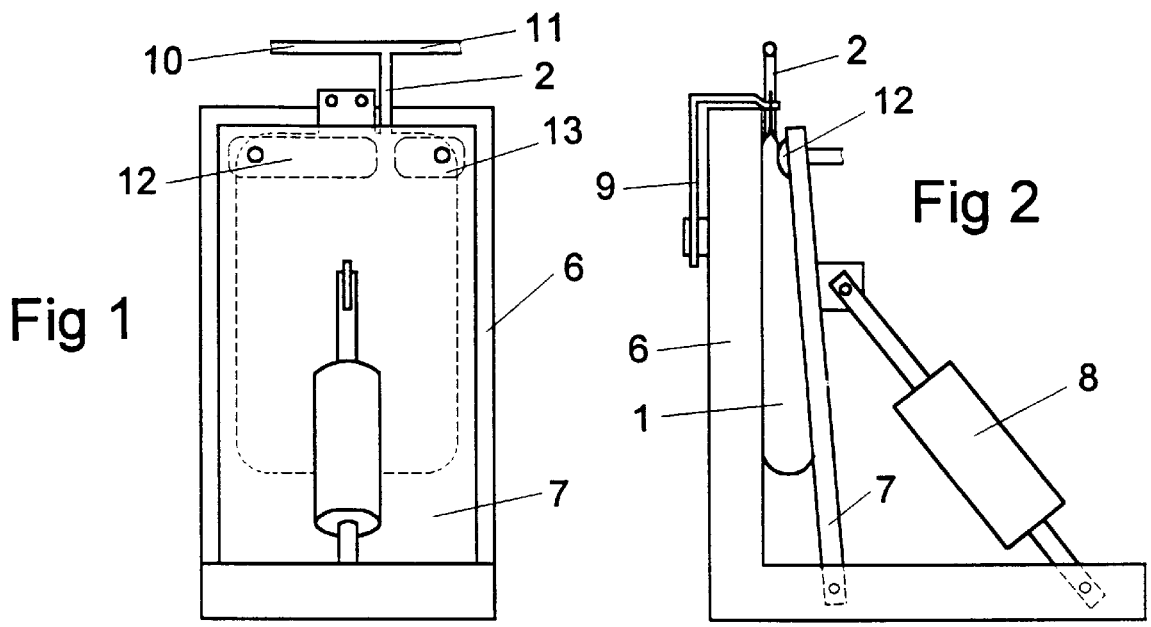
Fig 1
Fig 2
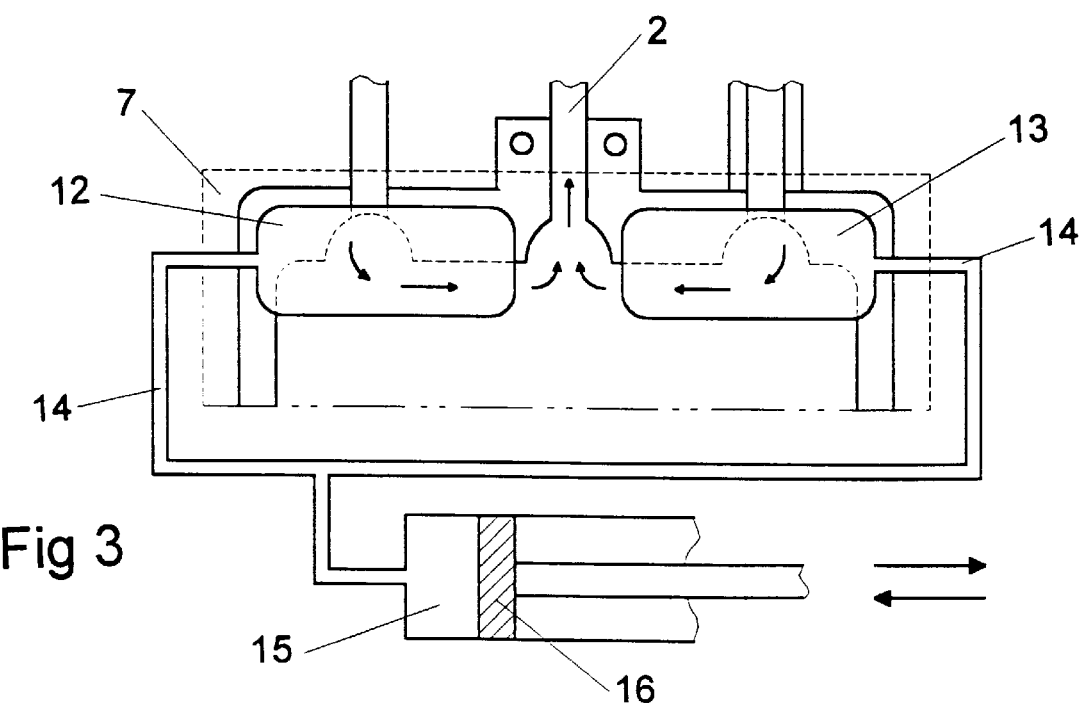
Fig 3
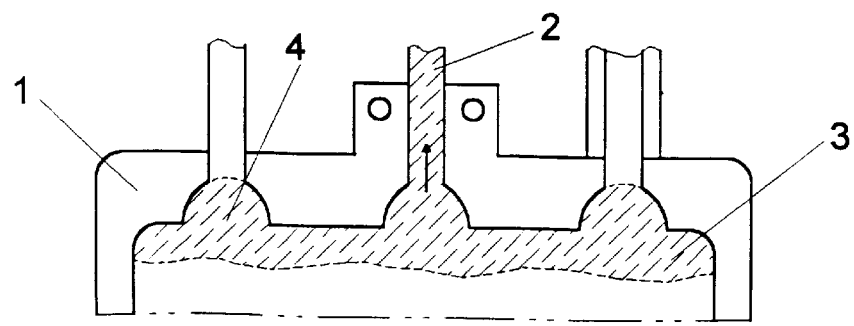
Fig 4

METHOD AND APPARATUS FOR HARVESTING BLOOD COMPONENTS

BACKGROUND OF THE INVENTION

1. Field of the Invention

The invention relates to blood component preparation. More specifically, the invention relates to a method and an extractor for pressing out plasma and buffy coat from a collapsible blood container, e.g. a blood bag, in which blood has been divided, by centrifugation, into a plasma layer, a buffy coat layer and a layer of red blood cells, the plasma and then the buffy coat being pressed out each through a separate outlet tube or through a common outlet tube, which is connected to the top of the blood container.

2. Description of the Related Art

In blood component preparation, blood is donated to a blood bag via a blood drawoff tube permanently connected to the bag. In addition, a number of side bags are connected to the blood bag by means of tubes. These connections are normally collected in the upper edge of the blood bag. Subsequently, the blood bag is centrifuged upright in a centrifuge cup, such that the blood forms layers, viz. an uppermost plasma layer, a subjacent buffy coat layer whose volume is relatively small, and a lowermost layer of red blood cells. At least the plasma and buffy coat fractions are then transferred to side bags by the blood bag being suspended at its upper edge in an extractor and subjected to mechanical pressure between a support surface and a pressure plate. The plasma then flows through an outlet tube over to a plasma container, while the buffy coat slowly flows upwards in the blood container. The outlet tube is normally branched into a plasma tube extending to a plasma container and a buffy coat tube extending to a buffy coat container but, alternatively, separate outlet tubes can be provided for each container. When the buffy coat has reached the top of the blood container, the plasma tube is closed and the buffy coat tube is opened. The major part of the buffy coat now flows over to the buffy coat container. However, a certain amount of buffy coat penetrates into the indentations formed by the various connections in the upper edge of the blood container, and there is a great risk that this amount remains in the blood bag after pressing-out. The remaining amount of buffy coat will mix with the red blood cell fraction and constitute a contamination therein. In manually operated extractors, one may manually press out these residues and feed them to the outlet tube, such that they can be pressed over to the buffy coat container. However, an efficient method of reaching these buffy coat residues in automatic extractors has not been available.

SUMMARY OF THE INVENTION

An object of the present invention is to provide a method and an extractor which yield a more complete discharge of the buffy coat fraction and, thus, a purer fraction of red blood cells.

The method according to the invention is characterised in that a pulsating pressure is applied to a top section or top portion or top portion of the blood container during the end phase of the pressing-out of the buffy coat. At this stage of the pressing-out operation, the buffy coat constitutes a narrow layer right at the very top at the edge of the blood container. The pulsating pressure gives the layer a pulsating motion and causes the buffy coat to be sucked out from said indentations in the edge of the blood container and flow freely towards the outlet tube for the buffy coat. This flow is additionally facilitated if the pulsating motion is not uniform along the entire width of the blood container but is designed so as to produce a pumping effect towards the outlet tube. Such a pumping effect can be achieved, for instance, by the pulsating pressure being applied on both sides of the connection of the buffy coat outlet tube to the top of the blood container.

The pulsating pressure can be produced in various ways. According to a preferred embodiment, use is made of one or more inflatable cushions abutting against the top section of the blood bag, and the pressure in said cushions is caused to pulsate at a certain selected frequency.

The inventive extractor, which comprises a stationary support surface and a movable pressing member between which the blood container is suspended and is subjected to a compressive force, is characterised by one or more inflatable cushions arranged on the support surface or pressing member or both on the same level as the top section of the blood container, and means for pulsating the pressure in said cushions.

BRIEF DESCRIPTION OF THE DRAWINGS

The invention will be further described below with reference to the accompanying Figures.

FIG. 1 is a front projection of an embodiment of an extractor according to the invention.

FIG. 2 is a side projection of the extractor in FIG. 1.

FIG. 3 illustrates on a larger scale a top section of an extractor with two inflatable cushions and a device for pulsating the pressure therein.

FIG. 4 illustrates a top section of a blood container at the end of the pressing-out of the buffy coat.

FIGS. 1 and 2 illustrate an embodiment of an extractor consisting of a base with a support surface 6 and a pressing member 7, which is movable towards the support surface and which, in this case, consists of a pressure plate. The pressure plate is operated by a pressure cylinder 8. Between the support surface and the pressure plate, a blood container 1 is suspended at its upper edge from a suspension hook 9. From the top of the blood container extends an outlet tube 2, which in the illustrated embodiment branches into a plasma tube 10 extending to a plasma container (not shown) and a buffy coat tube 11 extending to a buffy coat container (not shown). Alternatively, the plasma container and the buffy coat container can each have an outlet tube 2 which is connected to the top portion of the blood container. Moreover, there are usually additional connections to the top of the blood container, for instance, a closed blood draw-off tube and a tube extending to a SAGMAN container or the like. At the top of the inside of the pressure plate, on the same level as the top section or top portion of the blood container, two inflatable cushions 12 and 13 are arranged on both sides of the connection of the outlet tube 2 to the blood container.

FIG. 3 illustrates a top section of the extractor, where the pressure plate 7 for the sake of clarity is assumed to be transparent, such that the cushions 12 and 13 and the posteriorly situated blood container 1 are clearly to be seen. The blood container is here provided with three different connections in the top, and the intermediate connection concerns a common outlet tube 2 for plasma and buffy coat. The inflatable cushions are connected via conduits 14 to a cylinder 15, which is provided with a piston 16. By a reciprocating motion of the piston, the pressure in the containers can be caused to pulsate at a selected frequency and amplitude. By exposing the cushions to a varying pressure which is higher and lower than the pressure in the blood container, the blood container part abutting against the cushions will be alternately compressed and expanded. By the pulsating volume being small relative to the volume of the blood container, its motion will be affected but to a marginal extent. The basic pressure in the blood container is determined by the pressure exerted by the pressure plate 7.

FIG. 4 illustrates the top section of the blood container during the end phase of the pressing-out of buffy coat 3 through the outlet tube 2. There are indentations 4, in which the buffy coat tends to be stuck.

The extractor functions in the following manner: A centrifuged blood container, in which the blood has been divided into an upper plasma layer, an intermediate buffy coat layer and a lower layer of red blood cells, is suspended from the suspension hook 9 and compressed between the support surface 6 and the pressure plate 7. Plasma flows out through the outlet tube 2 and further through the plasma tube 10 to a plasma container. When the buffy coat layer has reached the upper edge of the blood container, the plasma tube 10 is closed, and instead the buffy coat tube 11 is opened. Buffy coat is pressed over to a buffy coat container and, during the final stage of this pressing-out, the pulsating of the pressure in the inflatable cushions 12 and 13 is started. The pulsating pressure applied to the top section of the blood container loosens the residues of buffy coat in the indentations 4 (FIG. 4) and these can flow out through the outlet tube 2. It has been found particularly efficient, as illustrated in the Figures, to perform the pulsation on both sides of the connection of the outlet tube 2 to the blood container. A suitable frequency of the pulsation can be 10–60 pulses/min. Especially good results are obtained in conventional blood bags when pulsating at a frequency of 20–40 pulses/min.

EXAMPLE

Comparative tests with and without pulsation were carried out when pressing out plasma and buffy coat from a number of centrifuged blood bags. The result appears from the following Table.

| Blood bag No. | Whole blood liter | Pulsation | BC liter | RBC liter | % WBC | % platelets |
|---|---|---|---|---|---|---|
| 1 | 0.490 | 20 pulses/min | 0.056 | 0.143 | 7.4 | 11.7 |
| 2 | 0.477 | 20 pulses/min | 0.033 | 0.136 | 8.8 | 12.2 |
| 3 | 0.518 | 30 pulses/min | 0.045 | 0.148 | 11.0 | 7.9 |
| 4 | 0.501 | 34 pulses/min | 0.044 | 0.189 | 15.8 | 14.2 |
| 5 | 0.545 | 34 pulses/min | 0.053 | 0.212 | 8.6 | 5.1 |
| 6 | 0.499 | 34 pulses/min | 0.054 | 0.157 | 10.1 | 6.5 |
| 7 | 0.552 | 40 pulses/min | 0.059 | 0.194 | 10.4 | 10.5 |
| 8 | 0.514 | 40 pulses/min | 0.054 | 0.169 | 10.3 | 9 4 |
| 9 | 0.535 | 40 pulses/min | 0.059 | 0.275 | 8.7 | 4.8 |
| 10 | 0.543 | 40 pulses/min | 0057 | 0.283 | 8.8 | 5.9 |
| 11 | 0.541 | 40 pulses/min | 0.061 | 0.318 | 10.5 | 5.9 |
| 12 | 0.498 | No | 0.046 | 0.155 | 17.6 | 33.8 |
| 13 | 0.489 | No | 0.046 | 0.149 | 26.5 | 30.1 |
| 14 | 0.537 | No | 0.043 | 0.184 | 33.6 | 80 |

%WBC states the proportion of the white blood cells in the blood donation that was found in the red blood cell concentrate (RBC). % platelets states the corresponding valve in respect of platelets. Thus, these values state to what extent the red blood cells were contaminated with white blood cells and platelets owing to residues of the buffy coat fraction. The Table shows that the pulsation according to the invion caused a considerably improved removal of the buffy coat fraction and, thus, a contamination of the red blood cells.

I claim:

1. A method for pressing out plasma and buffy coat from a collapsible blood container having a top portion to which at least one outlet tube is connected, and in which container blood has been separated into an uppermost layer of plasma, a subjacent layer of buffy coat and a lowermost layer of red blood cells, the method comprising:

pressing the plasma out of the blood container through the at least one outlet tube by compressing the blood container, whereby the buffy coat layer moves upwards in the container and into the top portion of the container; and, pressing the buffy coat out of the blood container through said at least one outlet tube by continued compressing of the blood container and applying a pulsating pressure to the top portion of the blood container during a final stage of the pressing the buffy coat.

2. The method of claim 1, wherein the pulsating pressure is applied to the top portion at two spots thereof, the spots being located on opposite sides of the at least one outlet tube at the top portion of the container.

3. The method of claim 1, wherein said pulsating pressure is produced by an at least one inflatable cushion which abuts against the top portion of the blood container, comprising inflating the cushion with a pressure fluid and pulsating the pressure of the fluid at a certain selected frequency.

4. The method of claim 3, wherein the pressure is caused to pulsate at a frequency of 10–60 pulses/min.

5. The method of claim 3, wherein the pressure is caused to pulsate at a frequency of 20–40 pulses/min.

6. An extractor for pressing out plasma and buffy coat from a collapsible blood container having a top portion to which at least one outlet tube is connected, and in which blood container blood has been separated into an uppermost layer of plasma, a subjacent layer of buffy coat and a lowermost layer of red blood cells, comprising:

a stationary support surface;

a movable pressing member;

a suspension device for suspending the blood container, with the top portion of the blood container positioned upwards, between said support surface and said pressing member;

means for moving said pressing member towards said support surface to compress the blood container and to press out the plasma through the at least one outlet tube and then to press out the buffy coat through the same or a different at least one outlet tube;

one or more inflatable cushions arranged on a limited area of said support surface or pressing member on a level with said top portion of the suspended blood container; and means for pulsating the pressure in said cushions at a selected frequency.

7. The extractor of claim 6, wherein said inflatable cushions comprises two cushions arranged to abut against said top portion of the blood container, the cushions located on opposite sides of the at least one outlet tube at the top portion of the container.

8. The extractor of claim 6, wherein said means for pulsating the pressure in said cushions comprises a reciprocating pump arranged in reciprocal fluid communication with said cushions.

\* \* \* \* \*